United States Patent [19]
Tozzi

[11] Patent Number: 5,916,226
[45] Date of Patent: Jun. 29, 1999

[54] APPARATUS AND METHOD FOR IMPROVED SUTURELESS ANASTOMOSIS

[76] Inventor: Piergiorgio Tozzi, Rue Cesar Roux 28/App. 44, Lausanne, Switzerland, 1005

[21] Appl. No.: 09/017,941

[22] Filed: Feb. 3, 1998

Related U.S. Application Data

[60] Provisional application No. 60/037,410, Feb. 3, 1997.
[51] Int. Cl.⁶ .................................................. A61B 17/00
[52] U.S. Cl. ........................................................ 606/153
[58] Field of Search ..................... 606/153, 154, 606/139, 151, 152, 213; 623/220, 1, 12

[56] References Cited

U.S. PATENT DOCUMENTS

| | | | |
|---|---|---|---|
| 4,233,981 | 11/1980 | Schomacher | 606/153 |
| 5,336,233 | 8/1994 | Chen | 606/153 |
| 5,346,501 | 9/1994 | Regula et al. | 606/151 |
| 5,540,701 | 7/1996 | Sharkey et al. | 606/153 |
| 5,609,626 | 3/1997 | Quijano et al. | 623/1 |
| 5,755,778 | 5/1998 | Kleshinski | 623/1 |

*Primary Examiner*—Michael Buiz
*Assistant Examiner*—Vikki Trinh
*Attorney, Agent, or Firm*—Gary M. Gron

[57] ABSTRACT

A device and procedure for suturless and wall-eversion free vascular and ducts anastomosis. The device comprises first and second annular emiprotheses formed to embrace and hold the ends of a pair of vessels or ducts. The emiprotheses are connected so that the vessel or ducts ends have a maximum exposure to blood in their interior.

17 Claims, 3 Drawing Sheets

APPARATUS AND METHOD FOR IMPROVED SUTURELESS ANASTOMOSIS

CROSS REFERENCE TO RELATED APPLICATIONS

This application claims prority based on co-pending provisional application serial number 60/037,410, filed on Feb. 3, 1997, entitled Device and Procedure for Sutureless and Wall -Eversion Free Vascular and Ducts Anastomosis, Piergiorgio Tozzi, inventor.

TECHNICAL FIELD

The present invention relates to anastomosis and more particularly to sutureless anastomosis.

BACKGROUND OF THE INVENTION

Common practice in surgical anastomosis consists in the use of stitches applied to the vessel's wall. Many attempts have been made to make anastomosis without stitches (sutureless). These particular techniques are called "mechanical anastomosis." They are based on the concept of folding the vessel's walls together ("wall eversion") and fasten them by a mechanical device. After about 10 years of research, this type of anastomosis has not been proven successful enough to be performed on human beings. The main problem experienced with "wall eversion" is the atrophy of the vessel walls folded together. The atrophy occurs because in the part of the wall that is folded (everted wall), the blood flow is significantly reduced.

Several particular techniques have been developed for sutureless repair of vessels. These techniques can be summarized in the following four categories:

a) stapling devices; b) metal rings ("Nakayama rings" and "Unililink" systems); c) heat-shrink tubing; and d) absorbable couplers.

The objective of all of these techniques has been to improve reliability, reduce required execution time and provide a less technically demanding procedure than the standard suturing together of the ends of severed blood vessels.

However, in order to avoid blood clots, all these techniques must rely on the principle of vessel wall eversion. This consists in folding the vessel's wall in a way that the inner part of the two vessels, called "intima", are smoothly abutting as shown (in FIG. 13 ref.: D. E. Mattox, J. J. Wozniak: "Sutureless Vascular Anastomosis with Biocompatible Heat-Shrink Tubing"; Arch Otolaryngol Head Neck Surg—November 1991, vol 117: 1260–1264). This technique reduces the risk of blood clotting, called thrombosis, by positioning the outer part of the vessel wall, called "adventitia" outside of the vessel area exposed to blood flow called "lumen".

The drawback of the above techniques is that once the vessel is folded, the inner part of vessel layers, called "intima", is no longer in contact with the blood flow through the vessel. This condition, as shown in several scientific papers (K. Nakayama, 1962; PI. Androsov, 1956; R. K. Daniel et al., 1984; J. J. Wozniak, 1985; L. T. Ostrup, 1986 and D. E. Mattox, 1991), and especially when applied to small diameter vessels, could cause the atrophy of the vessel wall involved in the suture. On the other hand, large diameter vessels, are not suitable for mechanical anastomosis because the vessel wall tends to rupture when folded.

SUMMARY OF THE INVENTION

Objects of the present invention are to:

a. Perform anastomosis of vessels of all sizes b. Reduce the risk of blood clots and atrophy of the vessel wall c. Reduce time required to perform the anastomosis d. Provide opportunity for less demanding technical procedures.

The above objects are achieved by apparatus for connecting first and second parts of a severed vessel or duct in end to end relationship. The apparatus comprises a generally annular first element positionable over the end of the first part of the vessel and having first and second opposed means extending generally axially from the end along the inner and outer walls of the vessel, at least one of the means being deformable towards the other means to embrace and hold the wall of the vessel. A generally annular second element is positioned over the end of the second part of the vessel and has first and second means extending axially from the end along the inner and outer walls of the vessel, at least one of the means being deformable toward the other means to embrace and hold the wall of the vessel. A means is provided for connecting the first and second elements so that the first and second parts of the vessel are positionable end to end without eversion.

In another form, the invention relates to a method for sutureless joining of several vessels in end to end relationship without eversion. The method comprises the steps of: positioning a first annular element having opposed inner and outer holding means extending from the end of one of said vessels along the inner and outer walls thereof; deforming the inner holding means of the first annular element outward toward the outer holdings means to embrace and hold the one vessel; positioning a second annular element having opposed inner and outer holding means extending axially from the end of the other of the vessels along the inner and outer walls thereof; deforming the inner holding means of the second annular element outward toward the outer holding means to embrace and hold the other vessel; and joining the first and second annular elements in end to end relationship so that the ends of the first and second parts of the vessel are connected in end to end relationship without eversion.

DESCRIPTION OF THE INVENTION

Figure 1:
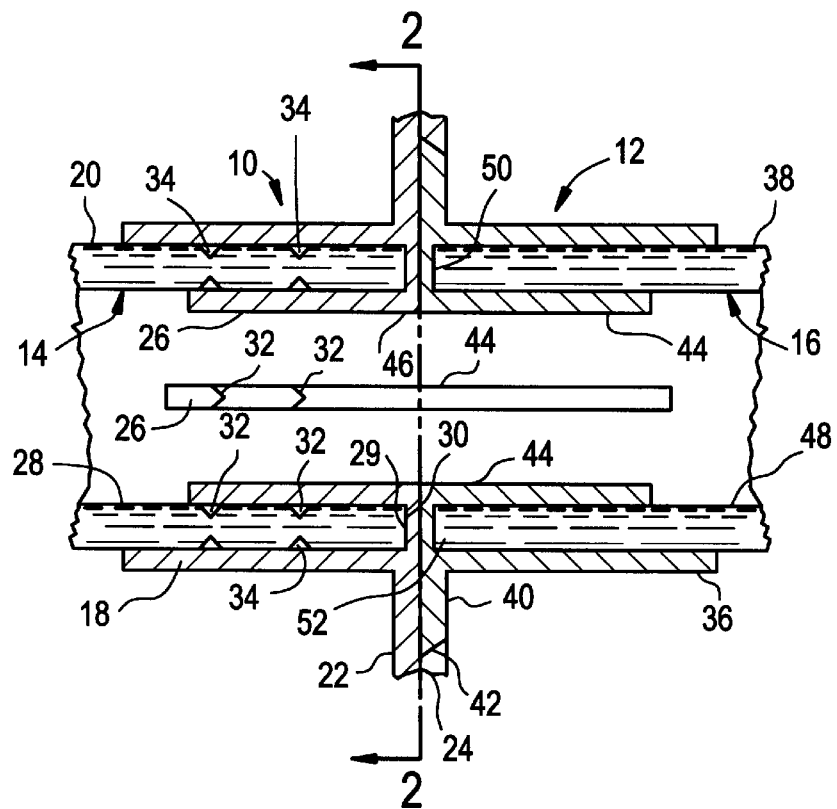
FIG. 1 illustrates a longitudinal section view of a sutureless anastomosis embodying the present invention.
Figure 2:
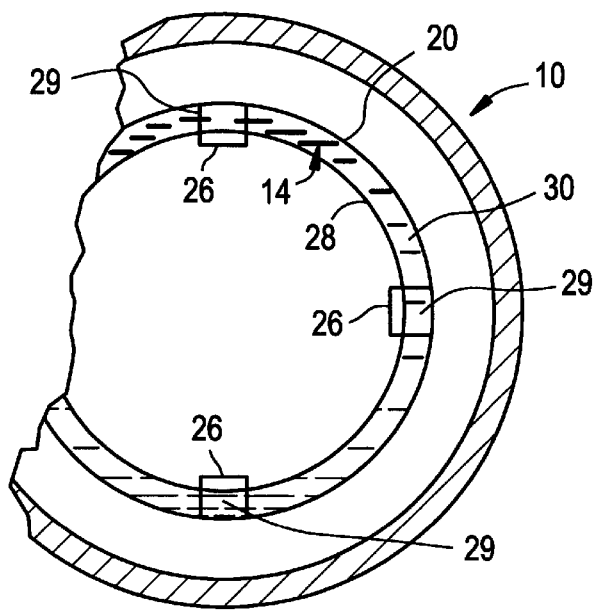
FIG. 2 is a cross-section view of FIG. 1 taken on lines 2—2 of FIG. 1.

FIGS. 1 and 2 illustrate one form of the present invention. The device comprises complementary parts 10, 12 (emiprothesis) that interlock to form a sealed, surface area providing continuity between two blood vessels 14, 16. Emiprothesis 10 comprises an outer annular element 18 received over the adventitia, or outer wall 20 of the blood vessel 14. An integral annular flange 22 extends radially outward from annular element 18. Flange 22 comprises an inwardly projecting outer lip 24 for connection purposes to be described later. A plurality of strips 26 extend axially from the plane of flange 22 along the lumen, or inner wall 28, of blood vessel 14. The strips 26 are connected to the inner diameter of annular element 18 by radially extending strips 29 integral with flange 22. It should be noted in FIG. 2 that the radial strips 26 cover but a small portion of the circumferential cross-sectional area of the end face 30 of blood vessel 14. The strips 26 are made of a material that is capable of being deformed outward toward outer annular element 18 to hold blood vessel 14 in an axial position. If necessary, projections on either the outer annular element 18 extending radially inward, or on strips 26, extending radially outward, provide an additional means for holding blood vessel 14 in an axial position. As described, the projections are in the form of triangular tabs 32, on strips 26 and triangular tabs 34 on annular element 18, both sets of which extend into blood vessel 14 to hold it. It should be apparent that single or multiples of projections 32, 34 may be used as needed.

Emiprothesis 12 comprises an outer annular element 36 received over the adventita, or outer wall 38 of blood vessel 16. An integral annular flange 40 extends radially outward from annular element 36. Flange 40 has an outer periphery beveled at 42 so that when flange 40 abuts flange 22, they are held together by lip 24 on flange 22 which is deformed to snap over the bevel 42 of flange 40 and therefore hold the flanges against one another. It should be apparent to those skilled in the art that other forms of holding the flanges 22 and 40 can be employed with equal success. A plurality of strips 44 extend axially from the plane of flange 40 along the lumen or inner wall 48 of blood vessel 16. The strips 44 are connected to the inner diameter of annular element 36 by radially extending strips 50, integral with flange 40. As with the radial strips 28, radial strips 50 cover but a small portion of the circumferential cross-sectional area of the end face 52 of blood vessel 16. This is an important feature because it exposes the intima, or internal portion of the vessels 14 & 16 to maximum internal blood flow.

In order to connect severed vessels, according to the present invention, the emiprothesis 10 & 12 use installed in the following manner. First the appropriate size is selected according to the nominal diameter of the vessel to be joined. As an example only, the diameter of the annular elements 18, 36 may range between 2 mm and 30 mm. The distance between the annular elements 18, 36 and strips 26, 44, respectively may range between 0.7 mm and 3 mm, depending upon the size of the vessel, the kind of vessel and the presence of possible diseases, such as atherosclerosis.

Figure 3:
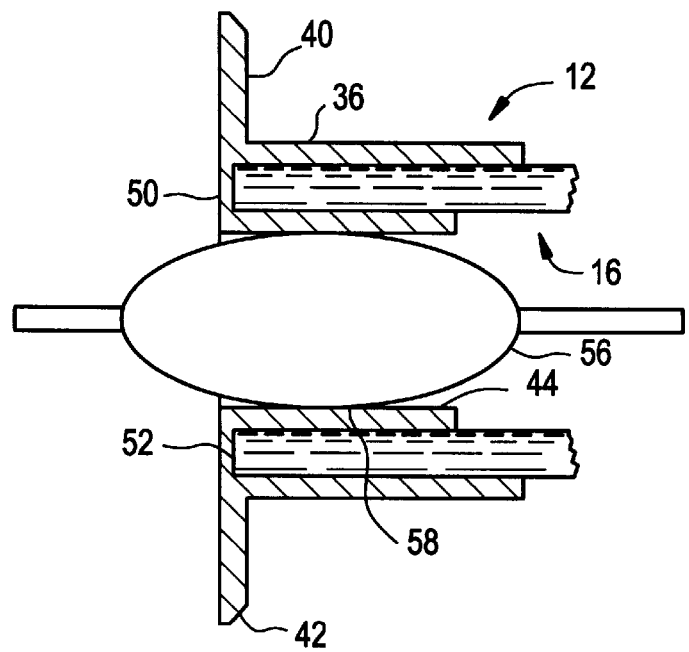
FIG. 3 is a longitudinal section view of the anastomosis of FIGS. 1 & 2 showing the installation of the device.

Once the correct size is selected, the emiprothesises 10 & 12 are slipped over the ends of blood vessels 14 & 16, respectively. The procedure for emiprothesis 12 and blood vessel 16 will be described. The procedure for emiprothesis 10 and vessel 14 is substantially identical. As shown in FIG. 3, the outer annular element 36 is slipped and inserted over the end of vessel 16 so that the vessel end face 52 abuts radial strips 50. If the condition of the vessel does not permit total insertion against strips 50, a blood compatible material, for example Fibrin, is used to close the gap.

Once this is done, the strips 50 are plastically deformed outward to hold the blood vessel 16 in place. As illustrated, this is accomplished by an angioplastic balloon 56 having an expandable outer diameter 58 which deforms strips 44 outward into blood vessel 16. The balloon 56 is removed and the same procedure repeated for emiprothesis 10 and 14. If necessary, adhesive can be applied to one or more of the strips or annular elements where they interface with the vessels. Once this is complete, flanges 22 & 24 are snapped together and the repair is ready for blood flow.

The materials constituting the device must have a suitable mechanical strength, a certain degree of plasticity and must be compatible with living organisms (bio-compatible). These characteristics require the inner cylinder to deform under pressure while the outer cylinder remains rigid, allowing the vessel wall to be compressed and held between the inner and outer annular elements and obtain a secure fastening of the device to the vessels. Materials such as stainless steels, plastics and ceramics may be employed. Also, elements with special coatings should be considered to accomplish all mechanical and bio-compatible requirements.

The material composition and the design of the outer cylinder must be such to guarantee enough rigidity so that the vessel wall could be compressed between two cylinders when the inner cylinder is expanded.

The design of the inner strips must be such to guarantee sufficient exposure of the vessel wall to the blood stream. This requirement is necessary to prevent the atrophy of the vessel wall. The actual construction of the inner cylinder, can be made of a discrete number of small strips described in FIGS. 1 and 2. Another construction of the inner cylinder, can be made by means of wire mesh as described in FIG. 4. In both cases, the inner cylinder surface element must be thin enough to be embedded into inner layer of the vessel wall (intima).

Figure 4:
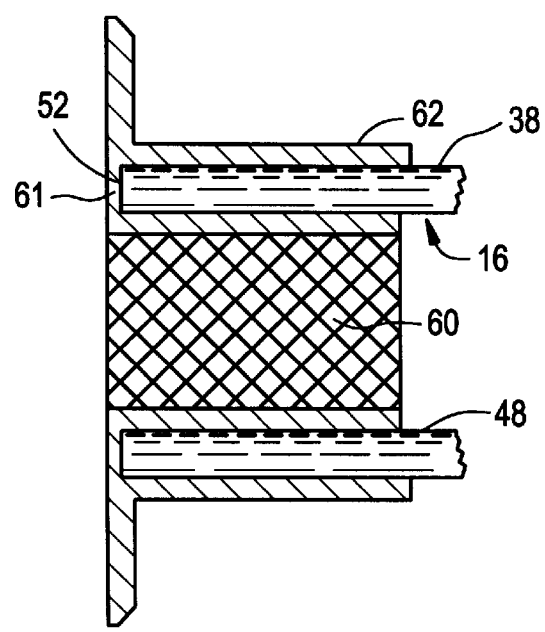
FIG. 4 is a longitudinal view of an alternate embodiment of the present invention.

Referring now to FIG. 4, an inner annular element 60 is formed from a wire mesh extending axially along the inner wall 48 of the vessel 16. An outer annular element 62 extends axially along the outer wall 38 of vessel 16. Radially extending portions 61 interconnect the wire mesh with the outer annular element 62 at the end 52 of vessel 16. Outer annular element 62 may be in the form of individual axially extending strips or a continuous annular cylinder. It should be noted that the wire mesh provides sufficient exposure of the interior wall 48 to blood flowing through the vessel. The same construction may be employed for the corresponding vessel to be attached to the end of vessel 16. In addition, the method of connecting the element to the corresponding element may be as shown in FIGS. 1 & 2 or by other appropriate means. Alternatively, the outer annular elements 18 and 36 of FIGS. 1 & 2 may be formed from wire mesh. In both cases the materials selected for the wire mesh and corresponding elements should have the characteristics outlined in the description of the embodiment of FIGS. 1 & 2.

Figure 5:
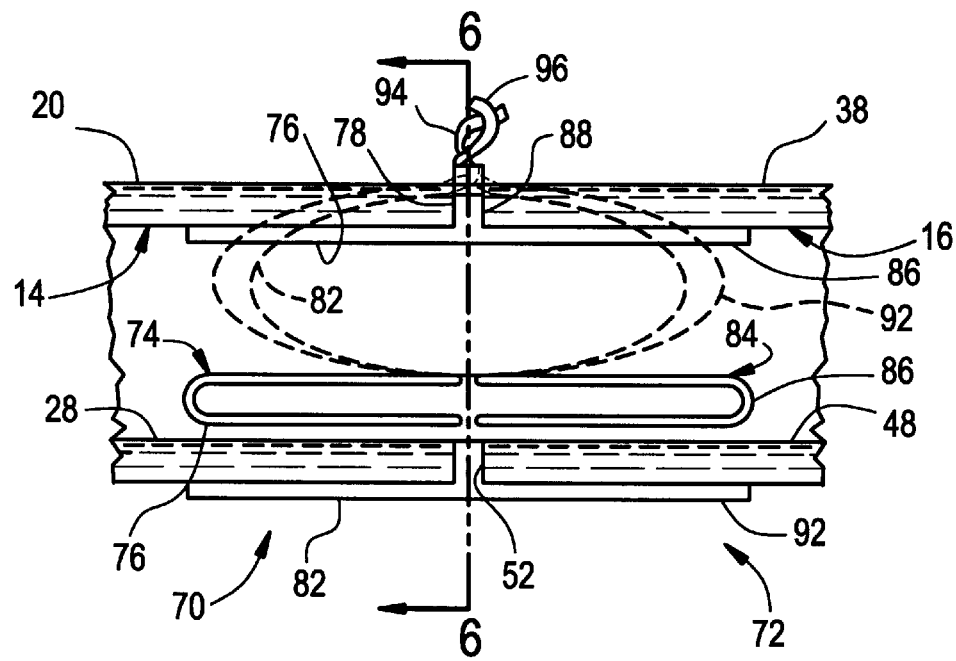
FIG. 5 illustrates a longitudinal section view of an alternative embodiment of the present invention.
Figure 6:
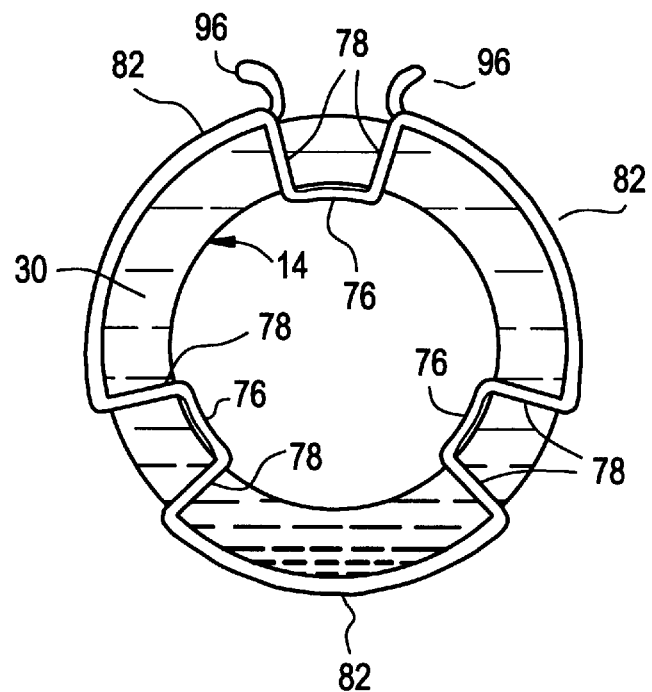
FIG. 6 is a cross-section view of FIG. 1 taken on lines 6—6 of FIG. 5.

Still another embodiment of the invention is shown in FIGS. 5 & 6. Emiprothesis 70 and 72 each comprise continuous strands of wire shaped to embrace the outer and inner walls of vessels 14 and 16. Emiprothesis 70 comprises a circuitous wire 74 having at least one inner loop 76 extending axially along the inner wall 28 of vessel 14. Inner loop 76 has integral radial sections 78 which connect with at least one integral outer loop 82 extending axially along the outer wall 20 of vessel 14. As is apparent from FIGS. 5 & 6, the inner and outer loops together embrace and hold the vessel 14 when one or both of the loops are deformed toward the other. In order to simplify the description of the invention, only three inner and outer loops are described. It should be apparent to those skilled in the art that additional numbers can be employed for enhanced holding. The emiprothesis 72 for vessel 16 is similarly constructed in that it comprises a circuitous wire 84 having at least one inner loop 86 extending axially along the inner wall 48 of vessel 16. Inner loop 86 has integral radial sections 88 which abut the end face 52 of vessel 16. Radial sections 88 connect with at least one outer loop 92 which extends axially along the outer wall 38 of vessel 16. As with the loops for emiprothesis 70, deformation towards one another holds the vessel 16 in place. Interconnecting hooks 94 and 96 provide a means for connecting the emiprotheses 70 and 72. The method for installing and deforming the emiprotheses of FIGS. 5 and 6 can be similar to that for FIGS. 1 and 2. It should be noted that the wire provides for maximum exposure of the vessels to blood for optimum establishment of leak free vessels.

The invention described above teaches a new method, and describes a devices suitable to perform surgical anastomosis without the use of stitches (sutureless) and without the folding of the vessels ("wall eversion"). The benefits obtainable by the use of this invention are as follows:

1. Offers a much simpler, less technically demanding, faster and reliable way to connect vessels and ducts in living organisms. This could significantly reduce the occurrence of post anastomosis vessel failures (i.e., clogging of the vessel, blood leakage, vessel deformation, etc.) especially in small diameter vessels.

2. Represents a valid alternative to the "mechanical anastomosis" by avoiding the atrophy caused by the folding of the vessel's wall (wall eversion).

3. Allows for video assisted surgical procedures which significantly reduce the size of surgical wounds required for the operation. This is accomplished with this invention by means of micro-device guided with external tools.

The invention presented in this disclosure additionally offers the opportunity to perform vascular anastomosis with video assisted surgical procedures and anastomosis of any type of duct in human body (i.e. ureter, urethra, deferent ducts, biliary and pancreatic ducts, trachea, bronchial tree, etc.)

Having described the invention, what is claimed as novel and desired to be secured by letters patent of the united states is:

1. Apparatus for connecting first and second parts of a severed vessel or duct in end to end relationship said apparatus comprising:

a generally annular first element positionable over the end of the first part of the vessel and having first and second opposed means extending generally axially from said end along the inner and outer walls of said vessel, at least one of said means being deformable towards the other means to embrace and hold the wall of said vessel;

a generally annular second element positionable over the end of the second part of the vessel and having first and second means extending generally axially from said end along the inner and outer walls of said vessel, at least one of said means being deformable toward the other means to embrace and hold the wall of said vessel, and means for connecting said first and second elements so that said first and second parts of said vessel are positionable end to end without eversion.

2. Apparatus as in claim 1 wherein the first of the holding means for each of said first and second annular elements is deformable outward toward the second of the holding means for said first and second elements.

3. Apparatus as in claim 2 wherein the second holding means for said first and second annular elements is generally cylindrical in shape.

4. Apparatus as in claim 3 wherein said second holding means for said first and second annular elements further comprises at least one inwardly directed projection for increasing the holding power of said second holding means.

5. Apparatus as in claim 3 wherein the second of the holding means for each of said first and second annular elements comprises at least one strip connected to said first of the holding means.

6. Apparatus as in claim 5 comprising a plurality of strips sufficiently spaced around the circumference of the first and second annular elements to permit substantial end to end contact between the ends of the first and second parts of the severed blood vessel.

7. Apparatus as in claim 6 wherein each of said first and second elements has said strips positioned at ninety degree intervals around the circumference of the first and second annular elements.

8. Apparatus as in claim 2 wherein said connecting means comprises:

a radially outwardly extending flange connected to said holding means on said first element, said flange being axially positioned substantially in line with the ends of the first part of the blood vessel, a radially outwardly extending flange connected to said holding means on said second element, said flange being axially positioned substantially in line with the ends of the second part of the blood vessel, and means on the periphery of said flanges for releasably connecting them in face to face relationship so that the first and second parts of the blood vessel are connected in end to end relationship.

9. Apparatus as in claim 8 wherein one of said flanges has a plurality of inwardly directed projections, said projections being flexible to permit the other of the flanges to be snapped into face to face relationship.

10. Apparatus as in claim 2 further comprising an adhesive on the radially inward side of the first holding means of said first and second elements for increasing the holding of the blood vessels.

11. Apparatus as in claim 1 wherein one of the first and second opposed means of said first and second generally annular elements is formed from a wire mesh.

12. Apparatus as in claim 1 wherein said first and second opposed means of the first and second generally annular elements comprise a substantially continuous wire having at least one loop extending axially along the inner wall of said vessel and an integral radially extending section abutting the end of said first and second parts of said vessel and at least one loop extending axially alond the outer wall of said vessel, said loops being deformable toward one another to embrace and hold said vessel.

13. Apparatus as in claim 12 wherein said means for connecting said first and second elements comprises at least a pair of hooks interconnectable with one another.

14. A method for sutureless joining of severed vessels or ducts in end to end relationship without eversion, comprising the steps of:

positioning a first annular element having opposed inner and outer holding means extending axially from the end of one of said vessels along the inner and outer walls thereof, deforming the inner holding means of said first annular element outward toward the outer holding means to embrace and hold said one vessel, positioning a second annular element having opposed inner and outer holding means extending axially from the end of the other of said vessels along the inner and outer walls thereof, deforming the inner holding means of said second annular element outward toward the outer holding means to embrace and hold said other vessel and joining the first and second annular elements in end to end relationship so that the ends of the first and second parts of the vessel are connected in end to end relationship without eversion.

15. A method as in claim 14 wherein said inner holding means of the first and second annular elements are deformed outward by an angioplastic balloon.

16. A method as in claim 14 comprising the further steps of placing an adhesive on the portion of the outer holding means of the first and second annular elements which contacts the outer wall of the first and second parts of the vessel before the annular elements are positioned thereon.

17. A method as in claim 14 wherein said first and second annular elements are snapped together.

* * * * *